(12) United States Patent
Metzger

(10) Patent No.: US 7,306,607 B2
(45) Date of Patent: Dec. 11, 2007

(54) METHOD AND APPARATUS FOR MINIMALLY INVASIVE DISTAL FEMORAL RESECTION

(75) Inventor: Robert Metzger, Wakarusa, IN (US)

(73) Assignee: Biomet Manufacturing Corp., Warsaw, IN (US)

( * ) Notice: Subject to any disclaimer, the term of this patent is extended or adjusted under 35 U.S.C. 154(b) by 442 days.

(21) Appl. No.: 10/628,793

(22) Filed: Jul. 28, 2003

(65) Prior Publication Data
US 2005/0027299 A1 Feb. 3, 2005

(51) Int. Cl.
*A61B 17/00* (2006.01)
(52) U.S. Cl. .................................................... 606/79
(58) Field of Classification Search ................ 606/79, 606/80, 82, 84, 87–89
See application file for complete search history.

(56) References Cited

U.S. PATENT DOCUMENTS

| | | | |
|---|---|---|---|
| 4,718,413 A | 1/1988 | Johnson | |
| 4,721,104 A | 1/1988 | Kaufman et al. | |
| 4,736,737 A | 4/1988 | Fargie et al. | |
| 4,892,093 A * | 1/1990 | Zarnowski et al. | 606/82 |
| 5,122,144 A * | 6/1992 | Bert et al. | 606/88 |
| 5,171,244 A | 12/1992 | Caspari et al. | |
| 5,228,459 A | 7/1993 | Caspari et al. | |
| 5,263,498 A | 11/1993 | Caspari et al. | |
| 5,364,402 A * | 11/1994 | Mumme et al. | 606/88 |
| 5,411,505 A * | 5/1995 | Mumme | 606/88 |
| 5,709,689 A * | 1/1998 | Ferrante et al. | 606/86 |
| 5,897,559 A * | 4/1999 | Masini | 606/86 |
| 5,902,272 A | 5/1999 | Eggers et al. | |
| 5,913,867 A | 6/1999 | Dion | |
| 6,468,280 B1 * | 10/2002 | Saenger et al. | 606/88 |
| 6,482,209 B1 | 11/2002 | Engh et al. | |
| 2002/0173797 A1 | 11/2002 | Van Zile et al. | |
| 2002/0198528 A1 | 12/2002 | Engh et al. | |
| 2002/0198530 A1 | 12/2002 | Sanford et al. | |
| 2003/0028196 A1 | 2/2003 | Bonutti | |
| 2003/0032971 A1 | 2/2003 | Hausmann, et al. | |

FOREIGN PATENT DOCUMENTS

| | | |
|---|---|---|
| GB | 2 358 822 | 8/2001 |
| WO | WO97/43985 | 11/1997 |
| WO | WO03/045256 | 6/2003 |

OTHER PUBLICATIONS

Partial European Search Report for EP 04 25 4123, Dec. 1, 2004.

* cited by examiner

*Primary Examiner*—Anuradha Ramana
(74) *Attorney, Agent, or Firm*—Harness, Dickey & Pierce, P.L.C.

(57) ABSTRACT

A tool assembly and a method for forming a less invasive resection of a selected bone portion. For example, a distal femur may be resected with substantially a single minor incision. Tools may be positioned through the single incision to resect a portion of the condyles of the femur. Generally, the medial condyle is resected followed by resecting a lateral condyles, but each condyle may be resected at a selected time through a single minor incision.

22 Claims, 4 Drawing Sheets ical portion of interest. For
METHOD AND APPARATUS FOR MINIMALLY INVASIVE DISTAL FEMORAL RESECTION

FIELD

The present disclosure relates generally to an apparatus and method for orthopedic surgery, and particularly to a method and apparatus for a less or minimally invasive distal femoral resection.

BACKGROUND

In the human anatomy, bones generally articulate or move relative to other bone portions. For example, the femur in the human anatomy articulates relative to the tibia in the human anatomy to form the knee joint.

Although a natural or normal anatomy generally allows for substantially smooth articulation of various portions, circumstances, such as, injury or age, may reduce the pain free and easy articulation of the various bone portions. Therefore, procedures, such as orthopedic procedures, may be performed to substantially repair and make more pain free articulations of the various anatomical portions.

Also, various other anatomical portions, such as other bone sections, may become weakened and need repair over time. Therefore, other procedures, such as, resection or removal of selected portions of the bone portion may be required. The resection generally prepares the bone portion for receiving a selected implant to allow for replacement or healing of the selected or injured bone portion. To repair a joint, such as a knee joint, resection of the various femoral and tibial portions is sometimes required. The portions are resected to receive a distal femoral implant to replace the condyles of the femur.

Generally, the resection of the bone portions requires significant access to the anatomical portion of interest. For example, the soft tissue must be pierced or cut to gain access to the bone portion which is underneath the soft tissue. Therefore, the soft tissue is cut and moved to allow access to the selected bone portion which causes trauma to the soft tissue. In addition, the tools necessary to resect the various portions are generally large in size and require the large openings.

Therefore, it is desired to provide a procedure which allows for substantially small incisions to perform the necessary procedures. It is further desired to provide surgical elements which allow for minimally or less invasive procedures and minimal trauma during a surgical procedure.

SUMMARY

An apparatus for providing a minimally invasive resection of a selected bone portion. Although the various instruments may be used for resection of various other bone portions, resecting a distal femoral portion disclosed herein is merely exemplary.

Also, a method for performing a minimally or less invasive procedure of distal femoral resection for a knee replacement. The resection being performed through a substantially minimally or less invasive incision through the dermis and other soft tissues to minimize trauma to the patient. Although the various techniques may be used in any other appropriate minimally invasive procedure for resecting a selected portion of the bone.

Further areas of applicability of the present invention will become apparent from the detailed description provided hereinafter. It should be understood that the detailed description and specific examples, while indicating the preferred embodiment of the invention, are intended for purposes of illustration only and are not intended to limit the scope of the invention.

BRIEF DESCRIPTION OF THE DRAWINGS

The present invention will become more fully understood from the detailed description and the accompanying drawings, wherein.

DETAILED DESCRIPTION OF VARIOUS EMBODIMENTS

The following description of various embodiments is merely exemplary in nature and is in no way intended to limit the invention, its application, or uses. Although the following description relates generally to a distal femoral resection, it will be understood that any appropriate bone portion may be resected using the following techniques and devices. Therefore, the discussion relating to the distal femoral resection is merely exemplary and is not intended to limit the appended claims or the scope of the description.

Figure 1:
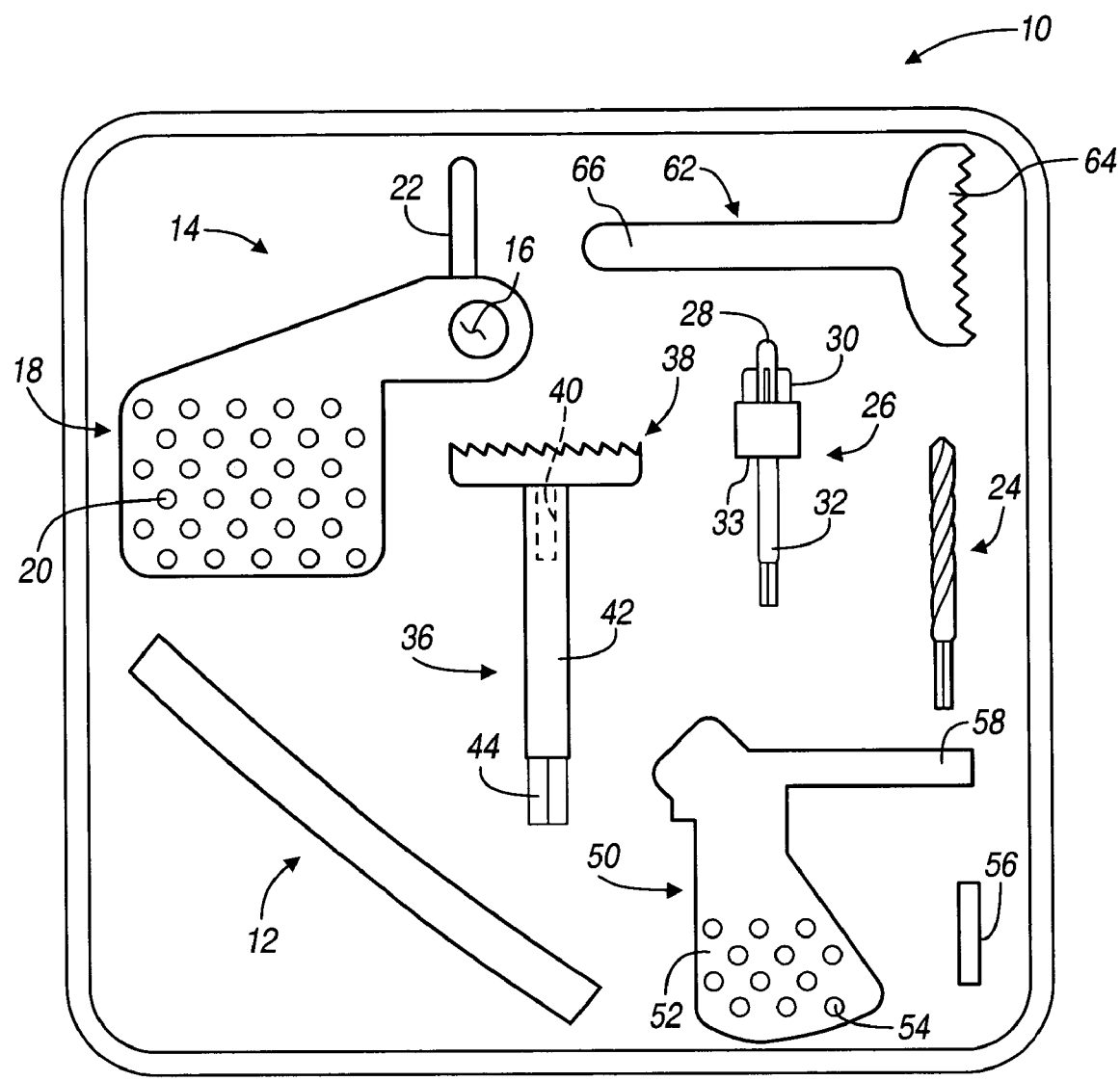
FIG. 1 is a plan view of an assembly of instruments for a procedure according to an embodiment.

With reference to FIG. 1, a system or assembly 10 for resection of a selected portion of a bone section or portion, such as a distal portion of a femur, is illustrated. The assembly 10 is illustrated to include a plurality of elements, as described herein. Nevertheless, it will be understood that the assembly 10 may be provided with more or fewer parts, and remain within the scope of the present disclosure. The elements illustrated are exemplary of the elements that may be provided for the assembly 10. Also, the assembly 10 may be provided in a pre-packaged kit that is ready and sterilized for a procedure.

The resection apparatus 10 generally includes a positioning rod 12 that may be positioned within an intramedullary portion of the bone section. Generally, the positioning rod is an intramedullary (IM) rod 12 that can be positioned in a selected portion of the bone to assist in fixation or stabilization of other appropriate portions. It will be understood that the positioning rod 12 may also engage any other appropriate portion of the bone. For example, the positioning rod 12 may be mounted to the bone using a clamp or received in a portion that is not the intramedullary portion of the bone. It is merely exemplary that the positioning rod 12 is an IM rod 12 and it may be used, for example, in a distal femoral reception.

Also provided is a drill or bit positioning guide 14. The drill guide 14 includes a first or positioning bore 16 that may be positioned relative to the IM rod 12, as described herein. Extending from the first bore 16 is a guide section 18 that defines a bore 20 and may define a plurality of the bores 20.

The guide section 18 extends from the first bore 16 in any appropriate manner. Thus, the guide bores 20 may be positioned relative to the positioning bore 16 and therefore relative to the IM rod 12. Extending generally perpendicular to the guide section 18 is a holding pin or rod 22. The holding rod 22, as illustrated herein, may be able to ensure that the incision formed through the soft tissue is kept open for manipulation of the various instruments internally. Generally, the holding rod 22 ensures that the soft tissue does not obstruct the view or the application of a tool relative to the guide section 18. It will be understood that the holding rod 22 need not necessarily affect the incision or the soft tissue around the incision. For example, the holding rod 22 may only hold the guide section 18.

A pilot boring tip or bit 24 is provided that has a diameter substantially equal to a diameter of one of the guide bores 20. Therefore, the pilot bit 24 is able to produce a pilot hole or bore 80 (FIG. 4) using the guide member 14. A spigot or reamer guide 26, is also provided that includes a distal end or tip 28 that is substantially equal in diameter to the diameter of the pilot bit 24. Extending circumferentially from the distal tip 28 is a fin 30. Although a plurality of the fins 30 may be provided, any appropriate number may be provided to substantially eliminate rotation of the spigot 26 after fixing the spigot 26. It will be understood that the fins 30 are not necessary as the rod 22 may be formed or positioned to not rotate. In addition, an amount of torque to rotate the rod 22 may not be applied. Extending proximally on the spigot 26 is a guide portion 32. Between the distal tip 28 and the guide portion 32 is a depth guide or shoulder 33. As described herein, the tip guide 33 allows for creating a selected depth of the reamed portion.

Also included in the assembly 10 is a reamer 36. On a distal end of the reamer is a reaming head 38. The reaming head 38 may include any appropriate structure to allow reaming of the bone structure. Defined in an internal portion of the reamer is a guide bore 40. The guide bore 40 is generally similar in diameter to the guide portion 32 of the spigot 26. Therefore, the guide portion 32 of the spigot 26 can pass into the guide bore 40 to guide the reamer 36. Extending proximally from the reaming head 38 is a shaft 42. The shaft 42 may terminate in a tool engagement portion 44 such that the reamer 44 may be engaged by an appropriate tool to ream a selected portion.

The assembly 10 further includes a saw guide 50. A first positioning portion 52 of the saw guide 50 includes at least a positioning bore 54 and may include a plurality of the positioning bores 54. A pin 56 can be positioned through an appropriate one of the positioning bores 54 to position the saw guide 50 in a selected position. The pin 56 may be passed into the bore, or other appropriate bore, such as one formed by the pin 56 during fixation. Extending at an appropriate position, and generally substantially perpendicular to the positioning portion 52 is a saw guide portion 58.

Also provided in the assembly 10 is a saw 62. The saw 62 includes a distal cutting head 64 and a proximal tool engaging portion 66. The saw 62 is generally substantially flat including a length that is substantially longer than a height. Therefore, the saw 62 may be provided through the saw guide 58 such that the saws guide 58 may generally guide the saw 62 in a selected cutting direction. Therefore, the saw guide 50 can be positioned with the pin 56 such that the saw 62 may be operated to be guided by the guide portion 58 to resect a selected bone portion.

With reference to FIGS. 2-6, a method of using the apparatus 10 will be described. It will be understood, however, that the method described herein is merely exemplary of the assembly 10 and not intended to limit the scope of the description or the appended claims. Although the following exemplary method relates to resection of a distal femoral portion, it will be understood that the assembly 10 may be used to resect any appropriate bone portion or section.

Figure 2:
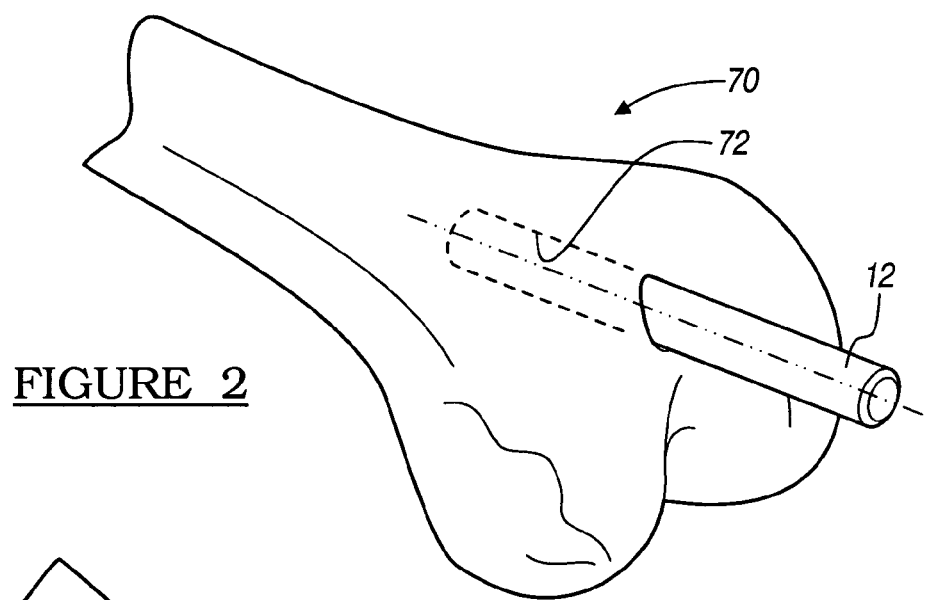
FIG. 2 is a perspective view of a distal portion of a femur including a positioning rod.

With particular reference to FIG. 2, the IM rod 12 is positioned in a selected bone section, such as a femur 70. The IM rod 12 is generally positioned in a bore 72 that extends along an intramedullary portion of the femur 70. It will be understood that the IM rod 12 may either be positioned in a pre-bored bore or may be a self-drilling IM rod 12. Therefore, the bore 72 may either be formed before the implantation of the IM rod 12 or substantially concurrently therewith. Nevertheless, the IM rod 12 is positioned in a distal portion of the femur 12.

The IM rod 12 is positioned relative to a first condyle 70a and a second condyle 70b. For example, the first condyle 70a may be a medial condyle of the femur 70 while the second condyle 70b is a lateral condyle of the femur 70. Therefore, the IM rod 12 can be positioned relative to the medial and lateral condyles of the femur 70. It will be understood that the IM rod 12 may be positioned in any appropriate manner.

Figure 2A:
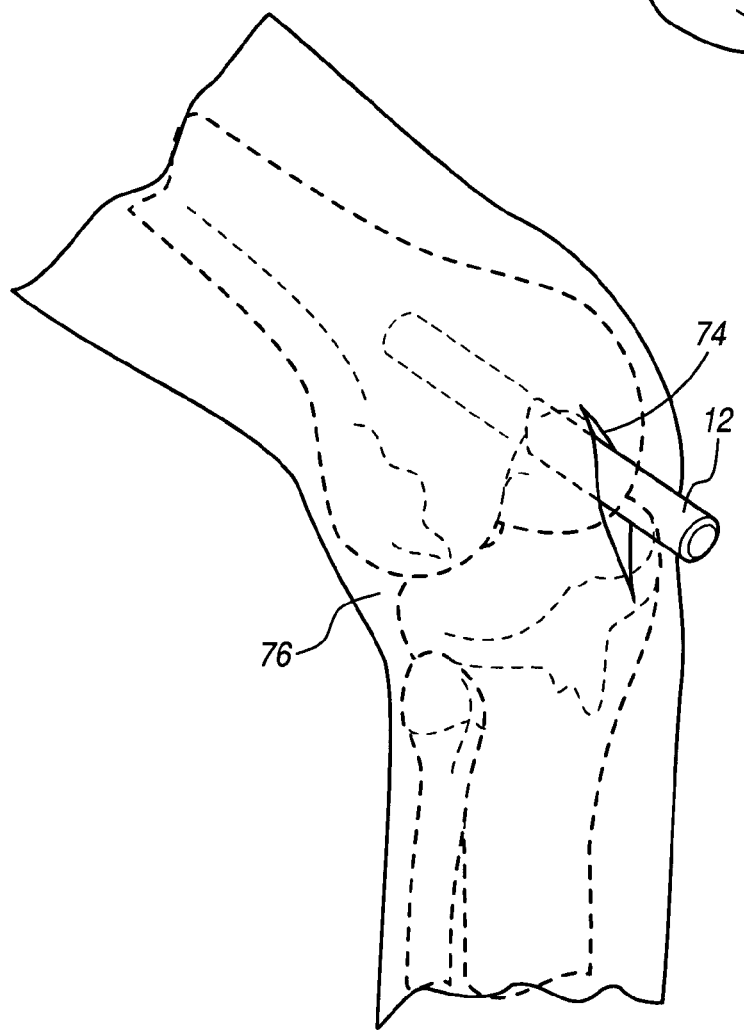
FIG. 2A is a perspective view of an incision made through soft tissue near a knee joint.
Figure 3:
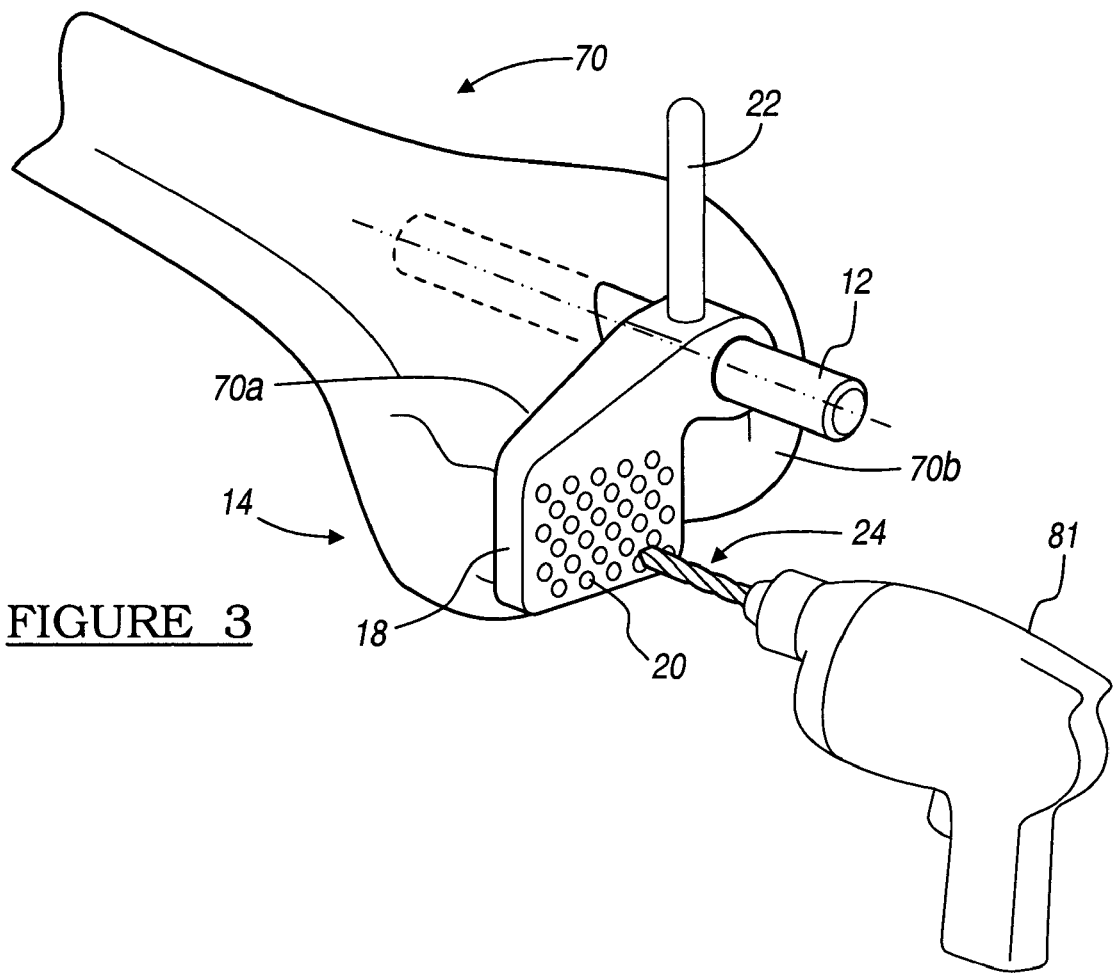
FIG. 3 is a perspective view of a distal portion of a femur including a guide.

With reference to FIG. 2A, this allows an incision 74 is made in a skin portion 76 generally near the distal end of the femur 70. The incision 74 may generally be substantially small, and only great enough to receive the various instruments and implants. Nevertheless, the incision 74 may be positioned generally near the distal end of the femur 70 and need not extend superiorly or inferiorly of this position. The incision 74 may be formed on any portion appropriate relative to the knee, but is generally made near the center or near the medial side of the femur 70. This allows the IM rod to be implanted substantially between the medial and lateral condyles 70a and 70b and the medial condyle 70a to be resected first.

Therefore, the IM rod 12 is positioned generally in the distal end of the femur 70. The incision 74 need only be made in this area of the leg. Nevertheless, it will be understood that any appropriate number or size of incisions may be used. For example, various other arthroscopic incisions may be used relative to the incision 74 to enhance viewing preciseness of the procedure. Nevertheless, the incision 74 may generally be provided at about 1 cm to about 10 cm in length.

After the IM rod 12 has been positioned in the bore 72, the drill guide 14 is positioned over the IM rod 12. The holding rod 22 is able to hold the incision 74, particularly the soft tissue surrounding the incision 74, such that the pilot hole bit 24 can be positioned relative to the drill guide 14. Nevertheless, as discussed above, the rod 22 need not necessarily hold the incision in a selected position. Any appropriate guide bore 20 in the guide portion 18 can be used to guide the pilot bit 24 into the distal femoral portion. Generally, the pilot guide bore 20 closest to the distal portion of the femur 70 is chosen to be drilled through. That is, the guide bore 20 generally closest to the distal portion of the femur 70 is used to guide the pilot bit 24 into the distal portion of the femur 70.

The bit 24 can be powered with any appropriate tool, such as a drill motor. Also, the bit 24 may be manually driven, with any appropriate hand tool through the appropriate guide bore 20. Nevertheless, the bit guide 14 is guided to guide the bit 24 to form the pilot hole 80 in the distal end of the femur.

Figure 4:
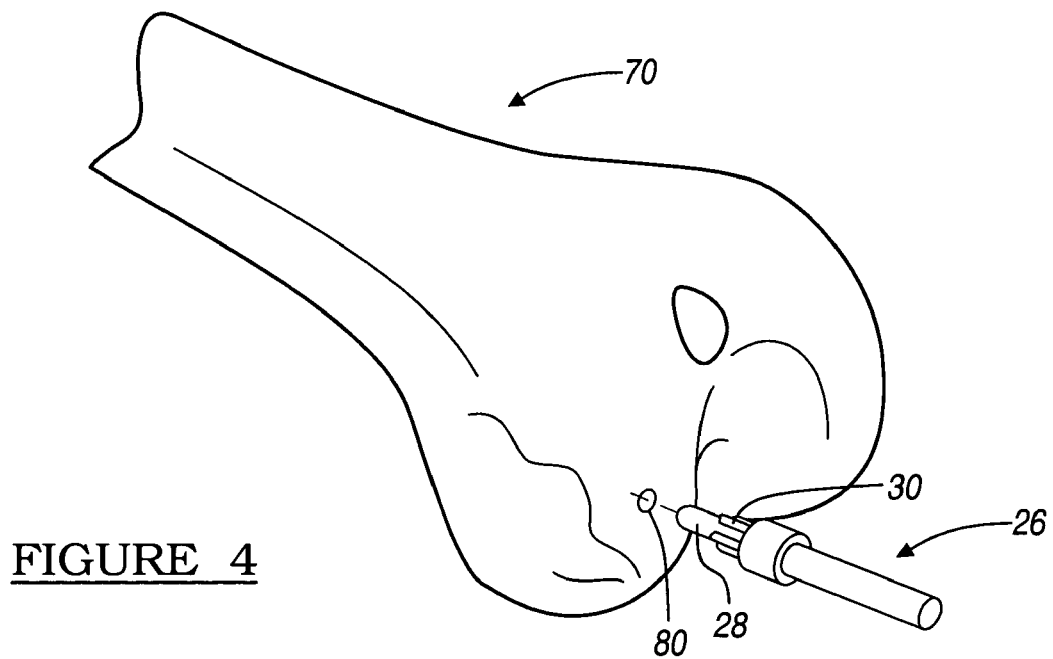
FIG. 4 is a perspective view of a distal portion of the femur including a second guide.

With reference to FIG. 4, after the pilot hole 80 has been formed in the femur 70, the spigot 28 may be positioned into the pilot hole 80. The positioning tip 28 and the fins 30 are driven into the pilot hole 80 to engage the spigot 26 therein. The spigot 26 may be positioned using any appropriate means, such as a hammer or impacting tool. The spigot 26 is positioned in the pilot hole due to the precise positioning of the pilot bore guide 14.

Figure 5:
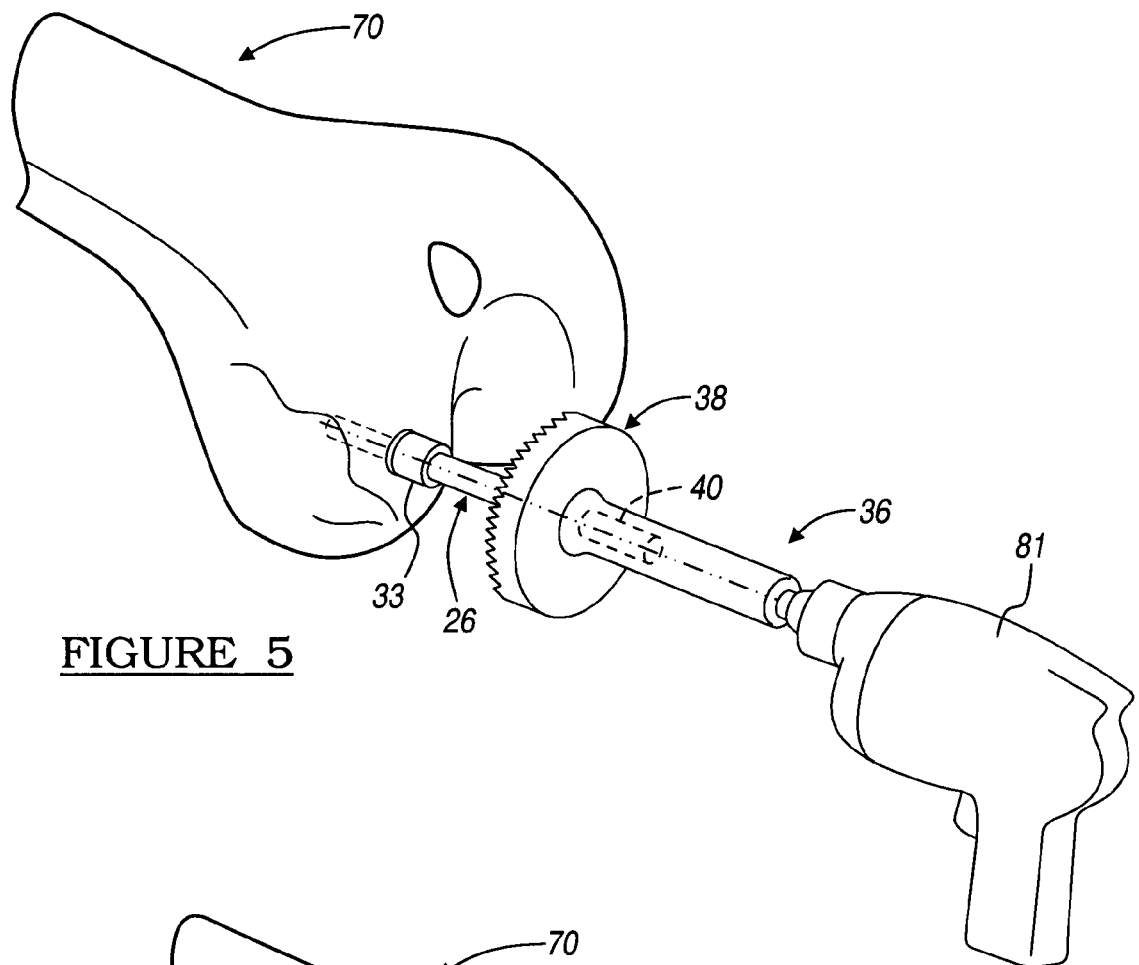
FIG. 5 is a perspective view of a distal portion of the femur including a tool that is guided.

With reference to FIG. 5, after the spigot 26 has been positioned or disposed in the pilot hole 80, the reamer 36 may be positioned relative to the spigot 26. After the reamer 36 is positioned relative to the spigot 26, an appropriate power tool or driver 81 may be used to power the reamer 36. For example, a drill motor may be used to rotate the reamer 36 to allow the cutting teeth on the head 38 to cut into a distal portion of the femur 70. The shoulder 33 on the spigot 26 acts as a stop for insertion of the reamer 36. That is, the shoulder 33 stops the movement of the reamer 36 towards the femur 70 before too much of the distal portion of the femur 70 is reamed. The reamer 36 is able to ream substantially all of the condyle. For example, the condyle being reamed may be the medial condyle of the femur 70.

Figure 6:
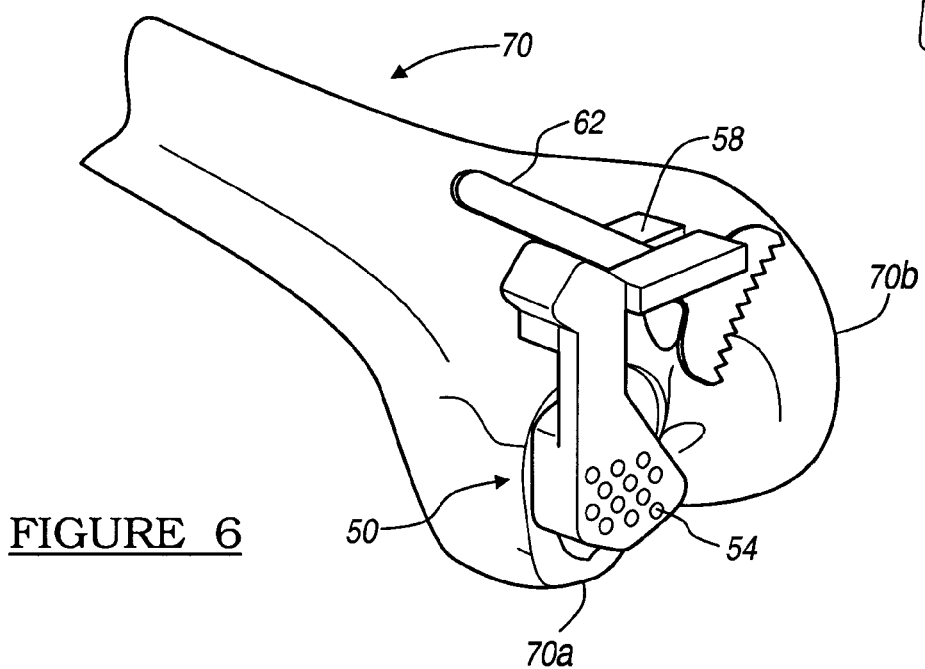
FIG. 6 is a perspective view of the distal end of the femur including a third guide.

With reference to FIG. 6, after the medial condyle 70a of the femur 70 has been reamed, the saw guide 50 can be positioned on the reamed portion of the femur 70. Generally, the pin 56 is positioned through a selected pin bore 54 such that the saw guide 50 is generally held in place. The pin 56 may be positioned into the pilot hole 80 to hold the saw guide in place. In this way, the guide portion 58 is positioned in an appropriate portion to guide the saw 62 to ream the portions of the femur 70. It will also be understood that the pin 56 may be positioned in any other bore, such as a bore formed by the pin 56.

The saw 62 is positioned through the guide portion 58 such that it contacts a portion of the medial condyle 70a or the lateral condyle 70b. Therefore, the saw guide 58 allows the saw 62 to ream a selected portion of the lateral condyle 70b relative to the medial condyle 70a. The saw guide 50 guides the saw 62 to resect a portion of the lateral condyle 70b substantially equivalently to the portion of the medial condyle 70a that has been reamed with the reamer 36. Therefore, generally equivalent portions of the distal portion of the femur 70 are reamed or resected using the assembly 10. In addition, the saw 62 may also ream a selected portion of the medial condyle 70a, such as the portion relative to the spigot 26.

Not only does the assembly 10 allow for substantially equivalent resection of both the medial and lateral condyles 70a, 70b of the femur 70, but also generally only one incision is used to resect both condyles of the femur 70. As illustrated above, the spigot 26 and reamer 36 allow for substantially minimally or less invasive reaming of the femur 70 through the single incision 74 relative to the medical condyle 70a. This allows for a substantially flat surface upon which the saw guide 80 can be positioned to allow for resecting the lateral condyle 70b. Therefore, the saw guide 50 can be positioned relative to the medial condyle 78 and guide the saw 62 relative to the lateral condyle 70b. The saw 62 is positioned relative to the saw guide 50 through the incision 74 near the medial condyle 70a which does not require expanding the incision 74. Therefore, the resection of the condyles of the distal portion of the femur 70 can be made through substantially a small single incision relative to the medial condyle 70a.

It will be understood, that resecting the distal portion of the condyle of the femur 70 may be an appropriate step in a total knee replacement. For example, after resecting the distal portions of the femur 70, the anterior and posterior portions may also be resected to allow for a distal femoral implant to be provided relative to the femur 70. It will be understood, however, that any other appropriate procedure may follow resecting the distal portion of the femur 70. Therefore, the assembly 70 may be used to resect the distal portion of the femur in preparation for any other procedure as a single procedure. Moreover, it will be understood that the assembly 10 will be used to resect any appropriate bone portion.

The assembly 10 is generally provided as a kit, such as distal femoral resection kit. Nevertheless, any portions of the assembly 10 may not be provided and may be selected on site by a physician or a person performing the procedure to substantially customize the kit to complete the assembly 10. Moreover, more than one of any of the portions of the assembly 10 may be provided for use by a physician. Although the drill guide 14 and the saw guide 50 have a number of portions to allow substantial selection by a physician during a procedure, a plurality may be provided to allow for even greater flexibility during a procedure. Therefore, it will be understood that the portions of the assembly 10 are neither completely inclusive nor completely necessary to be provided as a kit or may be provided as individual portions.

The description of the invention is merely exemplary in nature and, thus, variations that do not depart from the gist of the invention are intended to be within the scope of the invention. Such variations are not to be regarded as a departure from the spirit and scope of the invention.

What is claimed is:

1. A method of resecting a distal portion of a femur, comprising:
   forming an incision relative to a first condyle of the femur;
   forming a pilot bore relative to the first condyle;
   reaming the first condyle to form a first reamed portion; and
   resecting a second condyle of the femur with a saw that is guided using the first reamed portion;
   wherein reaming the first condyle and the second condyle is performed substantially through the incision.

2. The method of claim 1, further comprising:
   disposing a positioning rod relative to the femur;
   disposing a pilot bore forming guide with said positioning rod;
   wherein forming a pilot bore includes forming a pilot bore with said pilot bore forming guide.

3. The method of claim 2, wherein said pilot bore guide includes a selected pattern of pilot bore guide sections such that one of a plurality of pilot bores may be formed in the femur with a single positioning of said pilot bore guide.

4. The method of claim 1, further comprising:
   positioning a reamer guide in said pilot bore;
   wherein reaming the first condyle includes positioning a reamer relative to said reamer guide and reaming the first condyle.

5. The method of claim 1, further comprising positioning a tool guide relative to said reamed portion through said incision;
   wherein resecting a second condyle includes guiding a tool with said tool guide to resect the second condyle.

6. A method of resecting a selected bone portion comprising:
   selecting a first resection instrument;
   resecting a first portion of the selected bone portion a first amount with the first resection instrument;

selecting a second resection instrument that is different than the first resection instrument; and resecting a second portion of the selected bone portion a second amount generally equivalent to said first amount using said first resected portion and the second resection instrument wherein resecting said second portion includes guiding an instrument using said first resected portion such that said second portion is substantially equivalent to said first resected portion.

7. The method of claim 6, wherein forming said first resected portion includes resecting a selected condyle of a femur.

8. The method of claim 6, wherein forming said first resected portion includes resecting a selected condyle of a femur through a small incision such that access is minimized initially to the first condyle.

9. The method of claim 6, wherein forming a first resected portion includes:

positioning a reaming guide relative to said first portion of the selected bone portion; and guiding a reamer with said reaming guide to form said first resected portion.

10. The method of claim 9, wherein resecting a second portion includes:

positioning a tool guide relative to said first resected portion to guide an instrument for resecting said second portion.

11. The method of claim 6, wherein selecting the first resection instrument includes selecting a reamer instrument including a reamer head operable to grind the first amount.

12. The method of claim 6, wherein selecting the second resection instrument includes selecting a saw operable to cut the selected bone portion to remove the second amount.

13. A method of performing a less invasive bone resection procedure of a selected bone portion comprising:

forming an incision relative to the selected bone portion;

guiding a drill bit to form a bore with the drill bit;

reaming a first portion of the selected bone portion using a rotating reamer device to form a first reamed section; and guiding a saw blade to resect a second portion of the bone portion using the first reamed section.

14. The method of claim 13, wherein said forming an incision includes forming an incision about 1 cm to about 10 cm in length.

15. The method of claim 13, wherein said selected bone portion is a condyle of a femur.

16. The method of claim 13, further comprising:

forming a bore in the selected bone portion prior to guiding the drill bit;

disposing a spigot in the bore formed in the selected bone portion; and wherein reaming a selected portion includes reaming the selected bone portion by guiding the reamer with the spigot.

17. The method of claim 13, wherein the formed incision is the only incision used to access the selected bone portion to ream the first portion and resect the second portion.

18. A method of performing a bone resection procedure of a selected bone portion comprising:

reaming a first portion of the selected bone portion to form a first reamed section;

positioning a saw guide to engage the first reamed section; and guiding a saw blade with the positioned saw guide to resect a second portion of the bone portion relative to the reamed section;

wherein the first portion of the selected bone portion is a first condyle of a femur and the second portion of the selected bone portion is a second condyle of the femur to clarify Applicant's invention.

19. The method of claim 18, further comprising:

forming an incision relative to the selected bone portion, wherein reaming a first portion and guiding the saw blade both occur through the formed incision.

20. The method of claim 18, further comprising:

guiding a drill bit to form a bore with the drill bit;

positioning a spigot in the bore; and guiding a reamer with the spigot to ream the first portion.

21. The method of claim 20, further comprising:

interconnecting the saw guide with the bone portion via the bore.

22. The method of claim 18, wherein the second portion of the bone is resected only with the saw blade.

* * * * *

UNITED STATES PATENT AND TRADEMARK OFFICE
CERTIFICATE OF CORRECTION

| | | |
|---|---|---|
| PATENT NO. | : 7,306,607 B2 | Page 1 of 1 |
| APPLICATION NO. | : 10/628793 | |
| DATED | : December 11, 2007 | |
| INVENTOR(S) | : Robert Metzger | |

It is certified that error appears in the above-identified patent and that said Letters Patent is hereby corrected as shown below:

Title page item (57), Abstract; delete "condyles" and insert --condyle--

In column 3, line 61; delete "saws" and insert --saw--

In column 4, line 17; delete "12" and insert --70--

In column 5, line 54; delete "medical" and insert --medial--

In column 5, line 58; delete "78" and insert --70a--

In column 8, line 28; delete "to clarify Applicant's invention"

Signed and Sealed this

Twentieth Day of May, 2008

JON W. DUDAS
*Director of the United States Patent and Trademark Office*